US00PP18542P2

(12) United States Plant Patent
Meilland

(10) Patent No.: US PP18,542 P2
(45) Date of Patent: Mar. 4, 2008

(54) SHRUB ROSE PLANT NAMED 'MEIGGILI'

(50) Latin Name: *Rosa hybrida*
Varietal Denomination: Meigili

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 24 days.

(21) Appl. No.: 11/523,537

(22) Filed: Sep. 20, 2006

(51) Int. Cl.
*A01H 5/00* (2006.01)

(52) U.S. Cl. ..... Plt./106
(58) Field of Classification Search ..... Plt./106
See application file for complete search history.

*Primary Examiner*—Kent Bell
(74) *Attorney, Agent, or Firm*—Buchanan Ingersoll & Rooney PC

(57) ABSTRACT

A new and distinct variety of shrub rose plant is provided which forms in abundance on a nearly continuous basis in clusters attractive double cup-shaped fragrant blossoms which clean well that are bright peach in coloration. The vegetation is vigorous and a spreading round cover growth habit with procumbent vegetation is displayed. Attractive dark green foliage with a glossy finish is formed. The plant develops well regardless of the mode of asexual propagation. Excellent disease resistance with respect to Black Spot, Powdery Mildew, and Rust is displayed. The new variety is particularly well suited for providing attractive ornamentation in the landscape as a mass planting or when grown in containers.

2 Drawing Sheets

Botanical/commercial classification: *Rosa hybrida*/Shrub Rose Plant.
Varietal denomination: cv. Meiggili.

SUMMARY OF THE INVENTION

The new variety of *Rosa hybrida* shrub rose plant of the present invention was created by artificial pollination wherein two parents were crossed which previously had been studied in the hope that they would contribute the desired characteristics. The female parent (i.e., the seed parent) was the product of the cross of the 'Ruimired' variety (U.S. Plant Pat. No. 5,770) and the 'Paul Crampel' variety (non-patented in the United States). The male parent (i.e., the pollen parent) of the new variety was the product of the cross of the 'Korimro' variety (non-patented in the United States) and the 'Lady Gay' variety (non-patented in the United States). The parentage of the new variety can be summarized as follows:

('Ruimired'×'Paul Crampel')×('Korimro'×'Lady Gay').

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly forms in clusters attractive double cup-shaped fragrant blossoms which clean well that are bright peach in coloration, (b) exhibits a spreading ground cover growth habit with procumbent vegetation, (c) forms vigorous vegetation, (d) forms attractive dark green foliage with a glossy finish that contrasts well with the blossom coloration, (e) is highly resistant to Black Spot, Powdery Mildew, and Rust, and (f) is particularly well suited for providing attractive ornamentation in the landscape as a mass planting or when grown in containers.

The plant develops well following asexual propagation regardless of the mode of asexual propagation.

The new variety well meets the needs of the horticultural industry. It can be grown to advantage as ornamentation in parks, gardens, public areas, and in residential settings. The new variety is particularly well suited for growing in smaller areas as a ground cover, as a mass planting in a larger area, and in containers.

The new variety of the present invention also can be readily distinguished from its ancestors. More specifically, the 'Ruimired' variety forms dark red blossoms having no fragrance, the 'Paul Crampel' variety forms deep orange-scarlet blossoms, the 'Korimro' variety forms single light pink blossoms, and the 'Lady Gay' variety forms dissimilar orange-pink blossoms that tend to appear only once per season.

Additionally, the new variety can be readily distinguished from other similar rose varieties, such as the 'Meilmera' variety (U.S. Plant Pat. No. 10,002) and the 'Meidarin' variety (U.S. Plant Pat. No. 13,291). The 'Meilmera' variety has a similar growth habit, but displays white blossoms and is considerably less hardy. The 'Meidrain' variety also displays a similar growth habit, but displays vibrant orange blossoms and also is considerably less hardy.

The characteristics of the new variety have been found at Waso, Calif. U.S.A., and near West Grove, Pa., U.S.A., to be homogeneous and stable and to be strictly transmissible by asexual propagation, such as budding, grafting, and the rooting of cuttings from one generation to another. The new variety reproduces true to type by such asexual propagation.

The new variety has been named 'Meiggili,' and is being marketed under the PEACH DRIFT trademark.

BRIEF DESCRIPTION OF THE PHOTOGRAPHS

The accompanying photographs show, as nearly true as it is reasonably possible to make the same in color illustrations of this character, typical flowering plants of the new variety. The illustrated rose plants of the new variety were approximately three years of age and were observed during June while growing outdoors on 'Dr. Huey' rootstock near West Grove, Pa., U.S.A.

DETAILED DESCRIPTION

Figure 1:
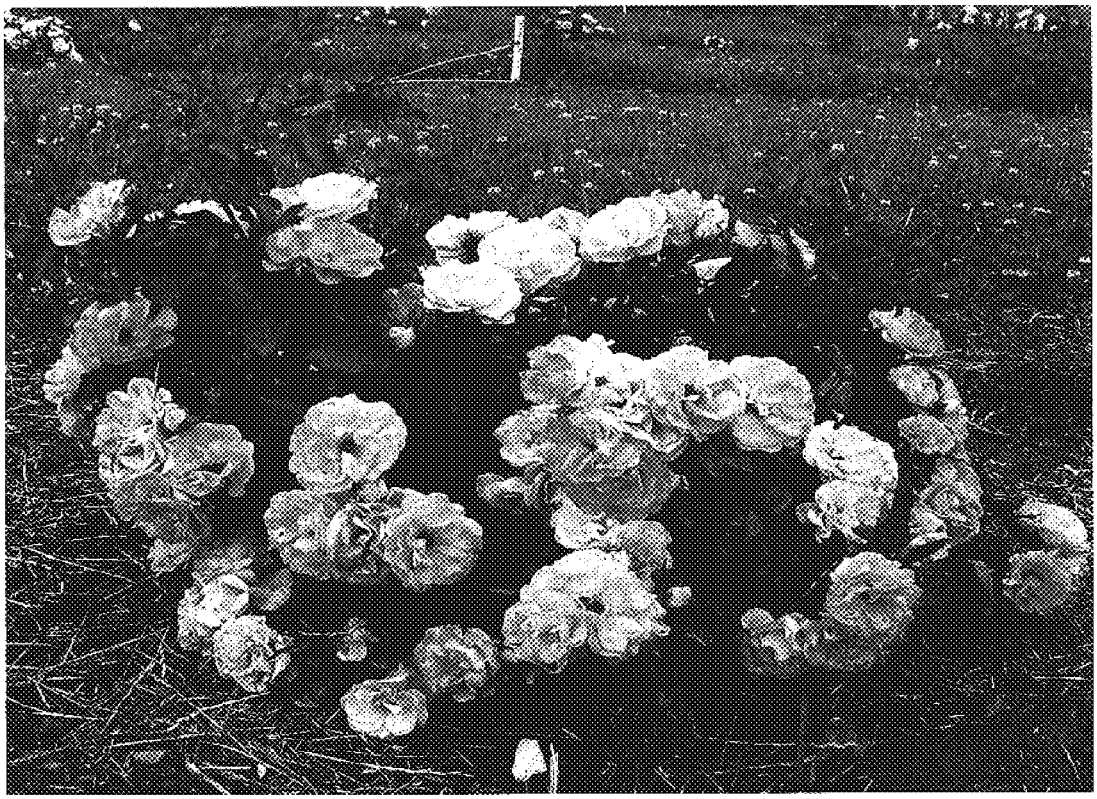
FIG. 1 shows a specimen of a flowering plant of the new variety wherein the spreading growth habit with procumbent vegetation is illustrated.
Figure 2:
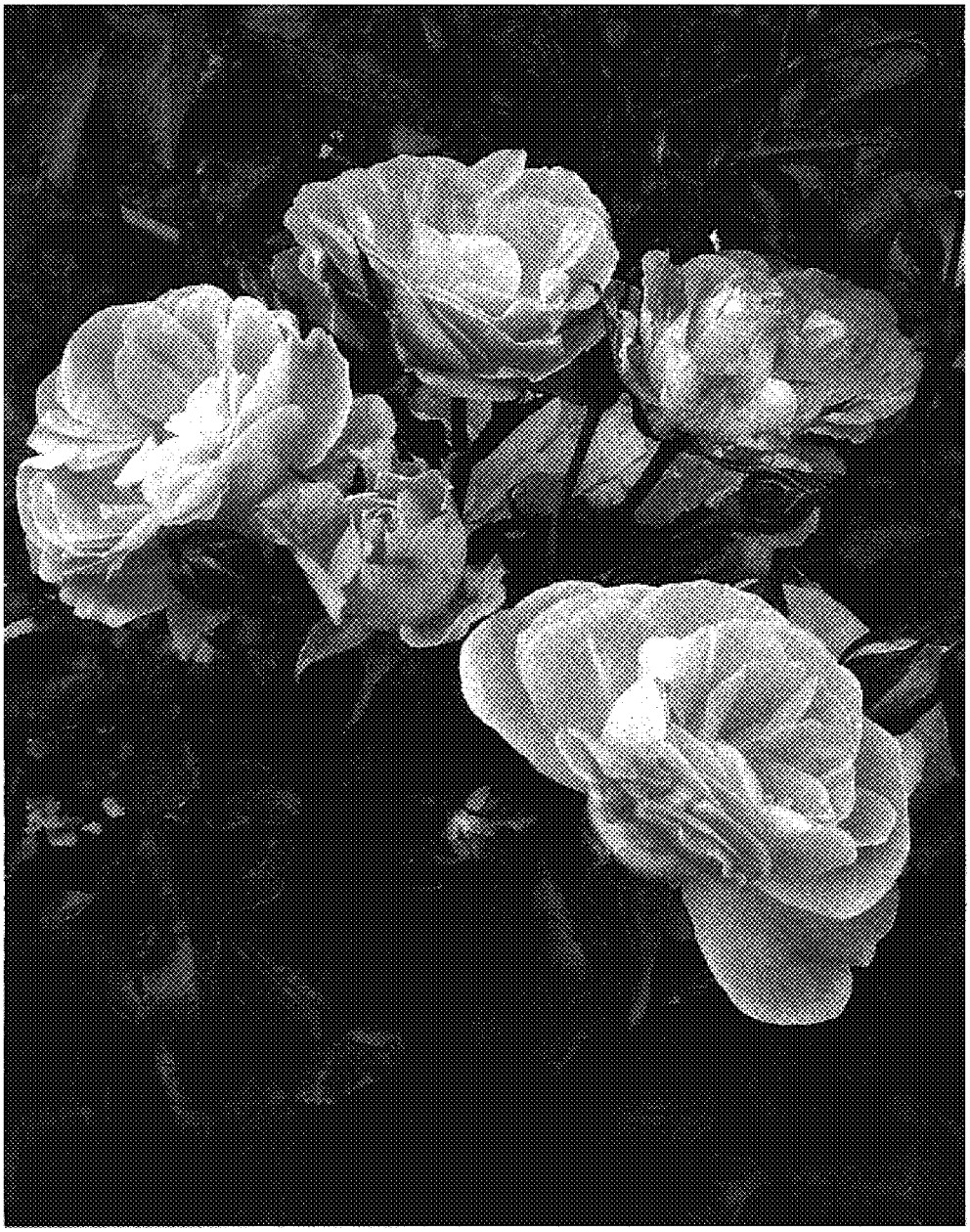
FIG. 2 shows a closer view where the buds, blossoms in various stages of development, and glossy dark green foliage are illustrated.

The chart used in the identification of colors is that of The Royal Horticultural Society (R.H.S. Colour Chart), London, England. The description is based on the observation of three-year-old specimens of the new variety during June while growing outdoors on 'Dr. Huey' rootstock near West Grove, Pa., U.S.A.

Class: Landscape Shrub.

Plant:

*Height.*—Approximately 25 to 35 cm on average at the end of the growing season.

*Width.*—Approximately 55 to 65 cm on average at the end of one growing season.

*Habit.*—As a low rounded mound.

Branches:

*Color.*—Young stems: Yellow-Green Group 144C with some highlights of Red Group 53C. Adult wood: Yellow-Green Group 144A.

*Thorns.*—Size: relatively small, approximately 1 cm in length on average. Configuration: commonly sharply pointed with the terminal point being nearly perpendicular to the stem and pointing upward. Quantity: approximately 4 to 5 on average over a length of 10 cm. Color: on young stems near Yellow-Green Group 151A, and on mature wood Brown Group 200D and more glabrous.

Leaves:

*Length.*—Approximately 7 to 8 cm on average including the petiole for a five-leaflet leaf, and approximately 9 to 10 cm on average including the petiole for a seven-leaflet leaf.

*Width.*—Approximately 5 to 5.5 cm at the widest point on average for a five-leaflet leaf, and approximately 7 to 7.5 cm at the widest point on average for a seven-leaflet leaf.

*Stipules.*—Approximately 20 mm in length, approximately 8 mm in width, Yellow-Green Group 144C with some Green Group 137A at the edges.

*Petioles.*—Approximately 24 mm in length on average, approximately 1.4 mm in diameter on average, and Yellow-Green Group 144C. in coloration.

*Leaflets.*—Number. Rarely 3, commonly 5, Typically 7, and rarely 9.

*Arrangement.*—Alternate and pinnate. Shape: elliptical to broadly elliptical, with a broadly acute to rounded apex and a base that typically is shortly attenuate. Margins: serrulate. Texture: glabrous on both surfaces, and papyraceus. Overall appearance: small, dense, medium green in coloration, and glossy. Color (young foliage): upper surface: near Green Group 137A. Under surface: near Green Group 138B with some Green Group 137C. Color (adult foliage): upper surface: near Green Group 139A. Under surface: near Green Group 138B with some Green Group 137C.

Inflorescence:

*Number of flowers.*—Commonly approximately 8 to 12 blooms on average in a cluster.

*Peduncle.*—Commonly approximately 25 to 30 mm in length on average, and approximately 1.5 to 2 mm. in diameter on average.

*Sepals.*—Five in number, lanceolate, approximately 21 to 22 mm in length on average, approximately 5 mm in width on average, near Green Group 143A in coloration on both surfaces, and with a sparse number of foliaceous appendages.

*Buds.*—Shape: generally ovoid. Size: very small. Length: approximately 1.5 cm on average as the calyx breaks. Width: Approximately 0.8 mm on average as the calyx breaks. Color (upper surface): as the calyx breaks Orange Group 25B towards the apex and Yellow Group 11B at the base. Color (under surface): as the calyx breaks primarily Yellow Group 11B.

*flower.*—Form: double. Shape: cup-like when fully open. Diameter: approximately 5 to 5.5 cm on average when fully open. Color (when newly open): upper surface: Orange Group 29C towards the apex and Yellow Group 11C at the base. Under surface: primarily Yellow Group 11C. Color (when fully open): Upper surface: Red Group 49A with a small amount of Yellow Group 11C at the base. Under surface: Primarily Yellow Group 11D. Color stability: there is a considerable degree of color change from the initial opening of the buds to the time of full blossom maturity. Fragrance: relatively mild. Petal form: obovate to narrowly obovate to narrowly obcordate. Petal number: approximately 25 to 30 on average under normal growing conditions. Petal texture: glabrous. membranceous, relatively thin, and semi-transparent. Petal margin: entire, but tends to be revolute to a slight degree. Petal apex: obtuse. Petal base: narrow cuneate. Petal size: commonly approximately 2.5 to 3 cm in length and approximately 2.3 to 2.5 cm in width. Petal drop: very good with the petals detaching cleanly before drying. Petaloids: typically approximately 1 to 3 per blossom, irregularly shaped, approximately 20 mm in length on average, and approximately 8 mm in width on average. Stamen number: approximately 55 to 60 on average, and regularly arranged about the pistils. Filaments: typically approximately 6 mm in length on average, and less than 1 mm in diameter. Pollen: near Yellow-Orange Group 22A in coloration. Pistils: typically approximately 30 in number. Styles: approximately 3 mm in length on average and less than 1 mm in diameter. Receptacle; slightly glaucous, approximately 2.5 to 2.8 mm in size on average when the flower is fully open, and near Green Group 138A in coloration. Hips: rarely observed. Lasting quality: the blossoms commonly last approximately 7 or 8 days on the plant, depending upon environmental conditions and approximately 5 or 6 days when cut and placed in a vase.

Development:

*Vegetation.*—Vigorous procumbent thin branches with thin upright shoots and a generally restrained growth habit.

*Blossoming.*—Abundant and nearly continuous.

*Resistance to diseases.*—Excellent with respect to Black Spot, Powdery Mildew, and Rust when compared to other commercial varieties under comparable growing conditions near West Grove, Pa., U.S.A.

*Hardiness.*—Grows well in U.S.D.A. Hardiness Zone No. 5. Resistance to heat presently is under evaluation.

*Formation of hips/seeds.*—Rarely observed.

I claim:

1. A new and distinct shrub rose plant characterized by the following combination of characteristics:

(a) abundantly forms in clusters attractive double cup-shaped fragrant blossoms which clean well that are bright peach in coloration, (b) exhibits a spreading ground cover growth habit with procumbent vegetation, (c) forms vigorous vegetation, (d) forms attractive dark green foliage with a glossy finish that contrasts well with the blossom coloration, (e) is highly resistant to Black Spot, Powdery Mildew, and Rust, and (f) is particularly well suited for providing attractive ornamentation in the landscape as a mass planting or when grown in containers;

substantially as herein shown and described.

* * * * *